United States Patent [19]

Park et al.

[11] Patent Number: 4,972,849
[45] Date of Patent: Nov. 27, 1990

[54] CONDOM (SANITARY CONTRACEPTION DEVICE)

[76] Inventors: Yong-Yeon Park, 27-3 Yeongdeungpo-dong 5-ka, Yeongdeungpo-ku, Seoul; Weol-Seon Suh, Sinsigaji Apt. 414-dong #902, 904 Mok-1-dong, Kangseo-ku, Seoul, both of Rep. of Korea

[21] Appl. No.: 257,743

[22] Filed: Oct. 13, 1988

[30] Foreign Application Priority Data

Oct. 15, 1987 [KR] Rep. of Korea ............... 1987-17550

[51] Int. Cl.[5] .................... A61F 6/02; A61F 6/04; A61F 5/00
[52] U.S. Cl. .................... 128/842; 128/844; 128/79; 128/918
[58] Field of Search .............. 128/842, 843, 844, 79; 604/347, 348, 349, 350, 351, 352, 353; 206/11 C

[56] References Cited

U.S. PATENT DOCUMENTS

| D. 246,117 | 10/1977 | Okamoto | 604/349 |
| D. 253,009 | 9/1979 | Okamoto | 128/844 |
| 2,410,460 | 11/1946 | Robinson | 604/349 |
| 2,433,538 | 12/1947 | Warner | 604/353 |
| 2,577,345 | 12/1951 | McEwen | 128/844 |
| 3,648,700 | 3/1972 | Warner | 604/349 |
| 4,320,752 | 3/1982 | Comparetto | 128/844 |
| 4,446,860 | 5/1984 | Gutnick | 128/844 |
| 4,726,359 | 2/1988 | Schroeder | 604/349 |
| 4,790,835 | 12/1988 | Elias | 604/349 |
| 4,795,425 | 1/1989 | Pugh | 128/844 |

FOREIGN PATENT DOCUMENTS

| 0348493 | 2/1922 | France | 604/349 |
| 0859835 | 12/1940 | France | 604/349 |

*Primary Examiner*—Robert A. Hafer
*Assistant Examiner*—Michael Brown
*Attorney, Agent, or Firm*—Michael N. Meller

[57] ABSTRACT

A new kind of condom provided with a cap is disclosed. The cap is integrally attached into an arcuate top portion of the main portion of the condom. This cap is protruded considerably long, and the bottom of the cap covers almost the whole area of the head portion of male sexual organ in order to protect the head portion from being subjected to sensitizations and stimulation. With the thus constructed condom the female sexual partner receives added pleasure because of the extended portion, and the male partner can prolong the sexual pleasure due to the ejaculation restraining effect of the cap. Therefore, the device according to the present invention brings sexual satisfaction to home life, and assures the successful execution of family planning, as well as preventing veneral diseases including AIDS.

1 Claim, 7 Drawing Sheets

FIG. 5
FIG. 6
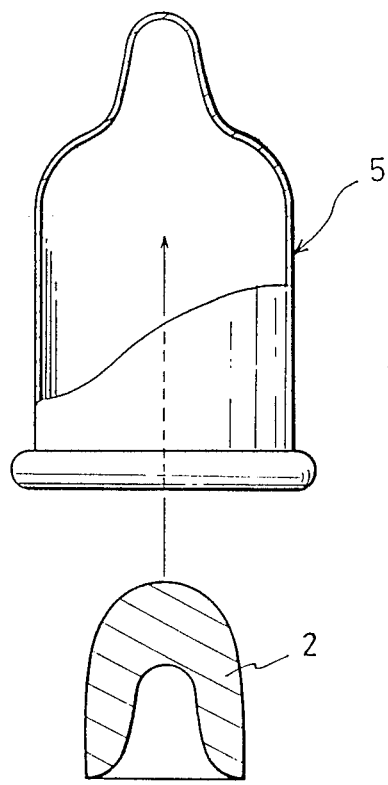
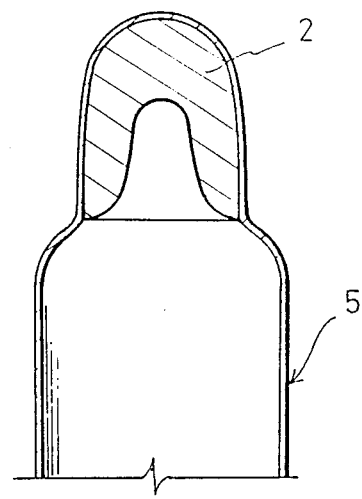

CONDOM (SANITARY CONTRACEPTION DEVICE)

TECHNICAL FIELD OF THE INVENTION

An aspect of the present invention relates to a condom as a sanitary contraceptive, the use of which making possible the inhibition of or protection against AIDS and various venereal diseases. Another aspect of the invention relates to a condom which has an ejaculation-restraining effect on the male during sexual intercourse or stimulation in order to promote the health of the male. These features may also be found together in the present invention, as well.

BACKGROUND OF THE INVENTION

Condom is the general name for a sanitary contraceptive, and the condoms known hitherto were devised in various patterns; however, these condoms do not exhibit the ejaculation-restraining effect on the male during sexual intercourse and some of them as shown in the accompanying drawings (FIGS. 14 and 15 as in Japanese Utility Model Laying-open Publication No. 86-4335) have special contours only for the sake of curiosity. Therefore, such condoms are not suitable for home or normal use.

Furthermore, the basic type of condoms as illustrated in FIG. 12 and 13, which are widely distributed among consumers, have not actively been used because they were made only for the contraceptive effect neglecting the curiosity. Especially, these kinds of condoms cannot give substantial help to the male in preventing a premature ejaculation. As a result, continued premature ejaculation causes sexual dissatisfaction in the female partner as well as undesirable sexual dreams.

Furthermore, with conventional condoms, a female partner cannot receive the masculine hormone discharged from the male partner so that the communication of feeling between male and female as taught by Chinese medicine cannot be achieved, thereby discouraging the habitual use of condoms.

SUMMARY OF THE INVENTION

The condom according to the present invention is provided with a protruded thick round portion at the tip of the main portion of the condom. The glans of the male sexual organ is contacted on the bottom of the thick protruded portion, and so is protected from sensitive frictions. This prevents the premature ejaculation of the male, and enables the male partner to successfully inhibit ejaculation in order to keep a healthy life. Further, in the case where the sexual organ of the male partner is too short, the condom according to the present invention provides the effect of lengthening the organ to provide added pleasure to the female partner, thereby removing the sexual dissatisfaction of the female partner.

Therefore, the device according to the present invention is useful for the balanced sexual life of married couples, and enables family planning to proceed smoothly through the communication of feeling provided by the features of the invention, at the same time enjoying sexual life, and preventing the female partner's dissatisfaction and thus undesirable sexual dreams.

It is an object of the present invention to provide a condom of improved structure with which a female may receive only masculine hormones from her male partner, thus permitting the communication of feeling between male and female as taught by Chinese medicine, while protecting the male sexual organ from being subjected to sensitizations which would result in premature ejaculation, as well as greatly reducing the possibility of contracting or transmitting venereal diseases, including AIDS.

Accordingly, the condom according to the present invention has the advantages of preventing undesirable sexual dreams, maintaining the health and well being of the male partner due to prevention of premature ejaculation, maintaining a healthy and happy marital life, and making it possible to practice family planning through the active use of the condom.

In order to attain to the above object and advantages, the present invention provides a relatively large arcuate top portion at the end of the main portion of the condom.

Inside the arcuate top portion, a cap is inserted, the cap being fitted to the inside of the arcuate top portion and the cap having a deep recess in it.

This cap is integrally attached to the inside of the arcuate top portion, and the inner wall of the cap can cover almost the whole area of the glans of the male sexual organ.

BRIEF DESCRIPTION OF THE DRAWINGS

FIG. 5 illustrates the process of applying the device of the present invention to a conventional condom;

FIG. 6 is a longitudinal cross sectional view of the product in which a conventional condom is combined with the device of the present invention;

DESCRIPTION OF THE PREFERRED EMBODIMENTS

The object and the advantages of the present invention will become more evident by describing the preferred embodiments of the present invention in more detail with reference to the attached drawings.

Figure 1:
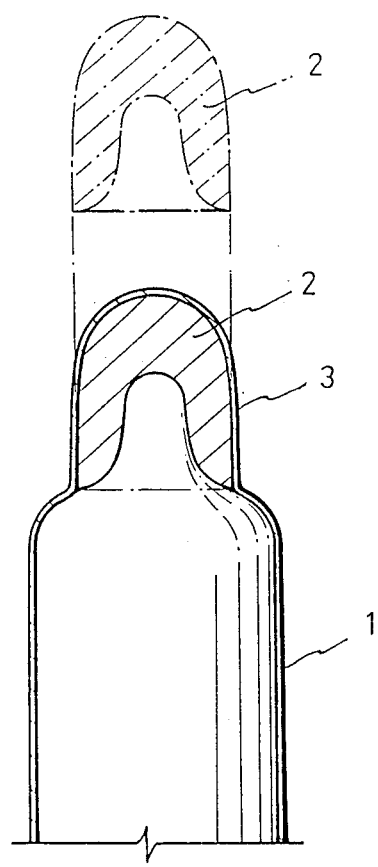
FIG. 1 is a partially cut-out perspective view of the device according to the pesent invention illustrating the process of the manufacturing.
Figure 2:
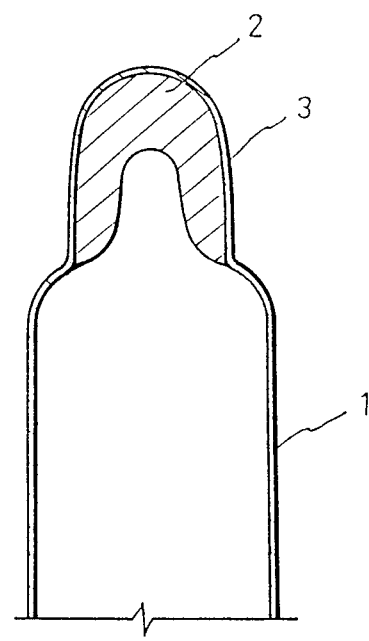
FIG. 2 is a longitudinal cross sectional view of the finished product of the present invention.

FIG. 1 illustrates an embodiment of the present invention, FIG. 2 is a cross sectional view of FIG. 1, FIG. 3 through 11 and FIG. 16 show other embodiments of the present invention, and FIG. 12 through 15 are selected examples of conventional condoms.

The device of FIG. 1 is the general type showing the embodiments of the present invention, in which an arcuate top portion 3 is formed on a cylindrical main portion 1, the diameter of the former being a little smaller than that of the latter. A cap is inserted into and integrally attached to the inside of the arcuate top portion 3, the outside diameter of the former being the same as the inside diameter of the latter. The cap 2 has a considerably thick wall with a deep recess on its center and is gently rounded at its bottom in order to cover almost the whole glans of the male sexual organ. The main portion 1 is made of a material containing latex, while the cap 2 is made of a soft material selected from those which do not give a harmful effect to the human body. The height of the cap 2 comes within the range of 10 mm to 30 mm, and there are various types of caps having different heights within the range.

Also, the cap 2 of the present invention may be applied to conventional condoms by forcefully inserting the cap into the tip portion of a conventional condom 5 as illustrated in FIG. 5 and 6.

The methods of making the condom utilize conventional techniques. These include dipping a phallic shaped mandrel of predetermined size, usually made of ceramic or steel, (which may be stationary or rapidly rotating about the longitudinal axis) into a warm bath containing a natural rubber latex.

A circumferential groove is located at the upper end of the mandrel. The mandrel is generally immersed in the latex bath to the top of the groove (i.e., so that the surface of the latex liquid is coincident with the top of the groove).

After a predetermined length of time the latex-coated mandrel is withdrawn from the latex bath. The latex coating in the mandrel is allowed to dry and, usually, a lubricant material is applied to the latex sheath.

A thickened ring of latex is formed at the upper (open) end of the condom. Starting from the upper portion the latex sheath is then rolled off the mandrel surface around the thickened latex ring to form a cup-shaped elastic ring of predetermined size and circumference.

In addition, in the present invention the mandrel is covered with the cap 2 before the mandrel dipping step, as shown in FIG. 1. After the mandrel and cap assembly is withdrawn, a latex coating conforming to the shape of the assembly is created and, after drying results in a latex sheath with an integral cap. Various types of caps may be applied to the mandrel to provide various embodiments of the capped condoms.

It should be noted that cap 2 which is a soft absorbent material, e.g., sponge, has an additional function, that of absorbing the ejaculated sperm. The cap 2 entraps the sperm and thus prevents or inhibits the transmission of venereal disease and AIDS to a greater extent than conventional condoms which, due to their thin walls may allow infected sperm to be transferred from the AIDS carrier.

Figure 16A:
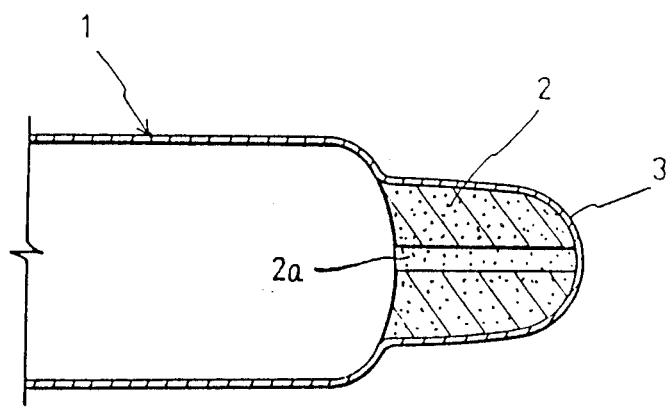
FIG. 16A is a longitudinal cross sectional view showing the flow path formed in the center of the cap of absorbent and FIG. 16B and 16C show embodiment wherein the arcuate top portion and the cap are both penetrated.
Figure 16B:
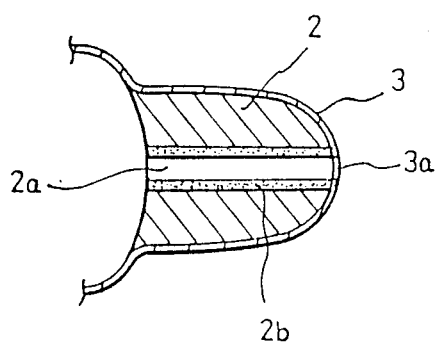
Figure 16C:
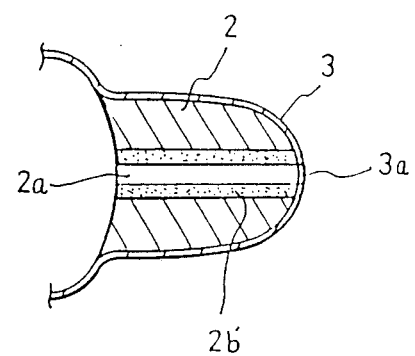

Referring to FIG. 16A, cap 2 has a slot 2a which is closed at one end thus providing an absorption tube but still allowing sperm entrapment. In the embodiments of FIGS. 16B and 16C, a slot is formed through the cap portion of the condom with the inner wall of the slot being coated with a spermicidal agent and/or venereal disease medication so that infertile seminal fluid is allowed to pass through. However, the transmission of AIDS is not completely prevented in this embodiment until an effective medication for treating AIDS is developed.

Figure 7:
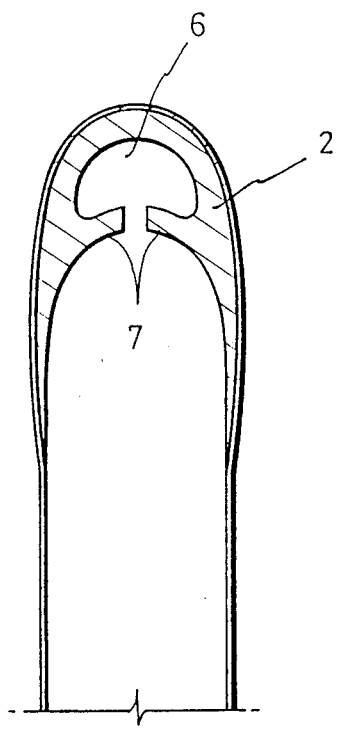
FIG. 7 through 11 show the various other embodiments of the present invention.
Figure 8:
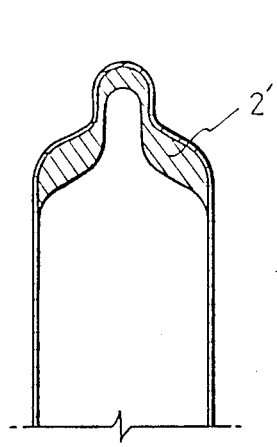
Figure 9:
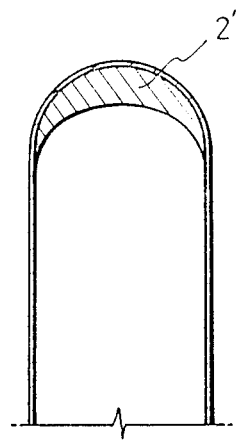
Figure 10:
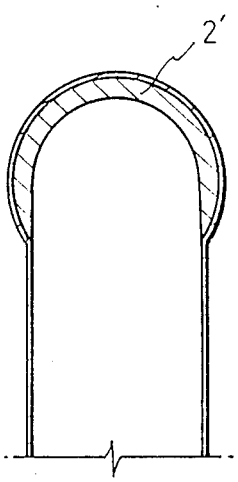
Figure 11:
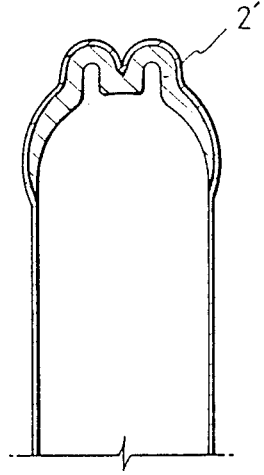
Figure 12:
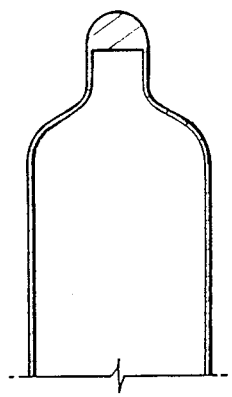
FIG. 12 through 15 show various types of conventional condoms.
Figure 13:
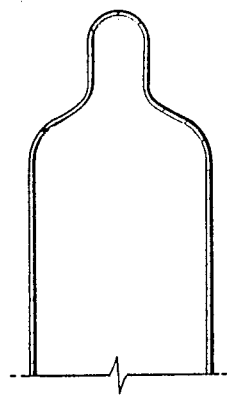
Figure 14:
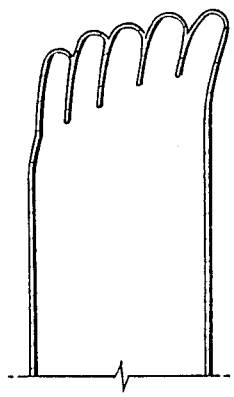
Figure 15:
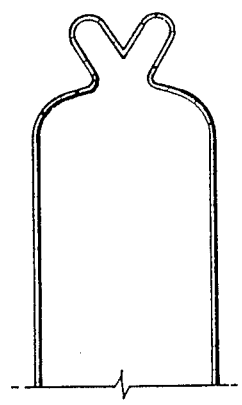

For males who have the tendency of especially premature ejaculation, an extension 4 may be provided at the bottom of the cap 2, so that it can completely cover the head portion of the male sexual organ to keep the sensitive portion of the male organ from being stimulated. Further, as shown by the embodiment of FIG. 7, the cap 2 can be provided with a cavity 6 and a partition 7 in order to double the soft elastic feeling and to give help to inhibiting or delaying ejaculation.

According to other embodiments of the present invention as shown in FIG. 8 through 11, various types of the cap 2' can be provided correspondingly to the various shapes of the tip of the main portion 1, as for as the cap can cover the whole area of the head portion of the male sexual organ.

A slot 2a may be formed in the cap 2 having a strong absorption force to provide an absorption tube for the ejaculation sperm passing through the slot, as shown in FIG. 16A.

Furthermore, the slot 2a may be extended through an opening 3a of the top portion 3 with a sterile agent layer 2b or 2b' being coated on the inner wall of the slot 2a as shown in FIGS. 16B and 16C. The sterile agent layer 2b or 2b' is comprised of a fertilization-restraining agent (for example nonylphenoxypolyethoxyethanol and dodecaethyleneglycol monolaurate) or a composition of said fertilization restraining agent and a sterilizing agent for treating bacilli in the vagina (for example VEGINAN, SUPPOSITORY, POBIDON JOD, and other various ingredients, such as antibiotics, antibacterials, trichomonacides and moniliacides). When the sperm is ejaculated into the slot 2a of the cap 2, the sperm is killed by the sterile agent layer 2b or 2b' while passing through the layer and then the killed sperm are permitted to enter the vagina naturally.

For example, and effective amount of nonylphenoxypolyethoxyethanol as a sperm-neutralizing agent is approximately 3.6–7.2 mg. In the embodiment of FIG. 16B, the sterilizing material is coated on the inner wall of cap slot 20, whereas the sterilizing and venereal medications preferably in the form of a mixture, coat the inner wall of cap slot 2a of FIG. 16C.

Therefore, the sterilization and treatment for the bacilli is also effected by the thus-constructed device. The slot 2a or the opening 3a is not limited to one but a plurality of them may be provided.

It should be noted that the type of anti-venereal medication is not critical and any suitable available drug for prevention of venereal disease may be used. An MIC dosage or prophylactic dosage may be used.

All the above described embodiments fall within the scope of the present invention, because they are intended to cover and protect with soft cushions the head portion of the male sexual organ. They are just variations of the standard device of the present invention.

Figure 3:
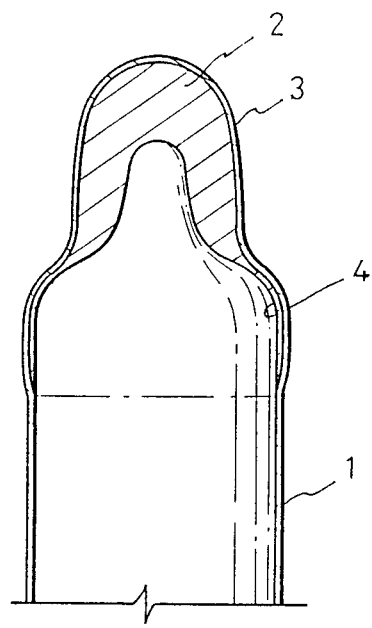
FIG. 3 is a partially cut-out perspective view of another embodiment of the present invention illustrating the process of the manufacturing.
Figure 4:
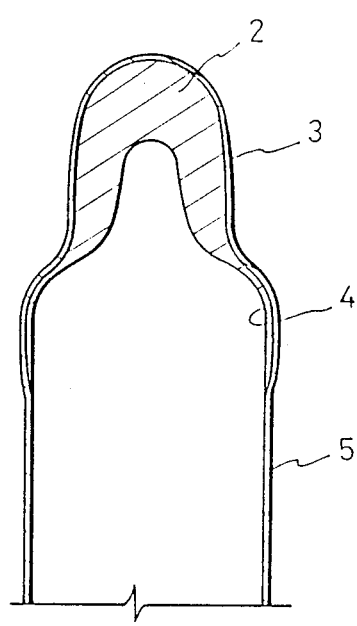
FIG. 4 is a longitudinal cross sectional view of the finished product of the device of FIG. 3.

The device of the present invention constituted as described above keeps the head portion of the male organ from being subjected to sensitizations and stimulation owing to the cap 2 of the present invention. This can bring the result of inhibiting the discharge of sperm and, consequently, such prevention of premature ejaculation can bring the effect of maintaining the good health of the male sexual partner in spite of frequent sexual intercourse, as taught by Oriental medical theory. Therefore, the device of the present invention provides a complete solution to the persons who are in difficulty because of premature ejaculation. Persons who especially suffer from premature ejaculation can use the type of condom which is shown in FIGS. 3 and 4, and in which the extension 4 of the cap 2 is formed. A protruded thick, round portion 2 at the tip of the condom may cover the sensitive glans of the male organ, thus dulling stimulation during coitus and effectively inhibiting or prolonging the time when ejaculation of the male takes place.

In the embodiment of the invention as shown in FIG. 7, the cavity 6 and partition 7 in the cap 2 will provide the space for the discharged sperm as well as a doubled soft feeling. The partition 7 is adapted to fit closely over the glans of the male sexual organ to dull the sensitivity and prohibit premature ejaculation.

Therefore, the device according to the present invention will provide for satisfied sexual life as well as preventing undesirable sexual dreams and, consequently, the device of the present invention will provide for a sustained happy home life in addition to an assured and reliable family planning aid.

What is claimed is:

1. A condom comprising a cylindrical main portion having a first wall portion thickness, an arcuate top portion formed on said main portion, the diameter of said arcuate top portion being a little smaller than that of said main portion and having said first wall portion thickness; and a cap with a predetermined thickness substantially greater than said first wall portion thickness inserted into and integrally attached to the inside of said arcuate top portion, said cap having a height greater than said predetermined thickness and having a deep inside central recess, the outside diameter of said cap being the same as the inside diameter of said arcuate top portion, the wall of said cap being gently rounded at its bottom portion in order to cover substantially the whole glans of the male sexual organ.

* * * * *